United States Patent [19]

Virgilio

[11] 4,132,676

[45] Jan. 2, 1979

[54] PERFUME COMPOSITIONS CONTAINING ETHYL 3,4-DICHLORO-5-ISOTHIAZOLECARBOXYLATE

[75] Inventor: Joseph A. Virgilio, Wayne, N.J.

[73] Assignee: Givaudan Corporation, Clifton, N.J.

[21] Appl. No.: 858,977

[22] Filed: Dec. 9, 1977

[51] Int. Cl.² ............................................... C11B 9/00
[52] U.S. Cl. .................................. 252/522; 260/302 R; 252/89R; 252/108; 252/305; 428/358; 424/64
[58] Field of Search ..................... 252/522; 260/302 R

[56] References Cited

U.S. PATENT DOCUMENTS

| | | | |
|---|---|---|---|
| 3,274,207 | 9/1966 | Kollonitsch | 260/302 R |
| 3,341,547 | 9/1967 | Mailey | 260/302 R |
| 3,769,040 | 10/1973 | Pittet | 252/522 |
| 3,876,652 | 4/1975 | Pittel | 252/522 |
| 3,907,819 | 9/1975 | Herkes | 260/302 R |
| 4,040,987 | 9/1977 | Shuster et al. | 252/522 |

*Primary Examiner*—Veronica O'Keefe
*Attorney, Agent, or Firm*—Thomas Cifelli, Jr.; Robert F. Tavares

[57] ABSTRACT

Ethyl 3,4-dichloro-5-isothiazolecarboxylate possesses a minty anise odor which is valuable in perfumery.

5 Claims, No Drawings

PERFUME COMPOSITIONS CONTAINING ETHYL 3,4-DICHLORO-5-ISOTHIAZOLECARBOXYLATE

BACKGROUND OF THE INVENTION

1. Field of the Invention

A novel odorant ester.

2. Prior Art

Ethyl 3,4-dichloro-5-isothiazolecarboxylate has not been described in the prior art.

THE INVENTION

The compound of the present invention has the following structure:

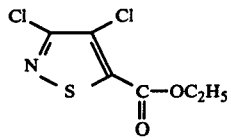

Its preparation is accomplished by reacting ethanol and the corresponding acid under esterifying conditions.

The ethyl 3,4-dichloro-5-isothiazolecarboxylate is valuable in perfumery because of its mild minty anise odor which is particularly useful as a light miscible note in a variety of perfumes.

The compound can be used in most fragrances in the ratio of about one to 70 parts per thousand of odorant bases containing the compounds larger quantities, e.g. 7-90 percent by weight of the formulation may be used to achieve special effects.

The odorant compositions containing the compound of this invention can be used as odorant bases for the preparation of perfumes and toilet waters by adding the usual alcoholic and aqueous diluents thereto; approximately 15-20% by weight of base would be used for the former an approximately 3-5% by weight would be used for the latter.

Similarly, the base compositions can be used to odorize soaps, detergents, cosmetics, or the like. In these instances a base concentration of from about 0.5 to about 2% by weight can be used.

The following examples are provided to illustrate further the practice of the present invention, but are for purposes of preferred embodiments only and should not be construed as limiting.

EXAMPLE I

Preparation of Ethyl 3,4-Dichloro-5-isothiazolecarboxylate 3,4-Dichloro-5-isothiazolecarboxylic acid (55 g; 0.278 mol) was dissolved in 500 ml of ethanol. The solution was saturated with hydrochloric acid and then refluxed for 3 hrs. The ethanol was distilled on a rotary evaporator leaving a residue which was then charged into 200 ml of water and neutralized with $NaHCO_3$. The water layer was extracted with 2x200 ml of $Ch_2CL_2$. The extracts were combined, dried over $MgSO_4$, filtered and the solvent distilled. The remaining liquid was distilled to yield 52.3 g (83%) of ethyl 3,4-dichloroisothiazol-5-carboxylate by 92° (3.0 mm).

Anal. Calcd. for $C_6H_5Cl_2NO_2S$: C, 31.89; H, 2.21; Cl, 31.36; N, 6.19; S, 14,20: Found: C, 32.17; H, 2.19; Cl, 31.14; N, 5.94; S, 14.42.

In a similar manner there was prepared the methyl ester (mp 42-43.5), the n-propyl ester (Bp 96° C. at 1.0 mm Hg) and the isopropyl ester (Bp 97° C. at 3.0 mm). None of these had the minty anise type odor of the claimed compound.

EXAMPLE II

Use of Ethyl 3,4-Dichloro-5-isothiazolecarboxylate as an Odorant

The following examples are used to illustrate the use of ethyl 3,4-dichloro-5-isothiazolecarboxylate in perfume formulations.

| A. Woody Base | Parts per thousand |
|---|---|
| Methyl Ionone | 50 |
| p-tert-Butylcyclohexyl Acetate | 50 |
| Methyldihydrojasmonate | 70 |
| Cedryl Acetate | 100 |
| Sandalwood Oil E.I. | 200 |
| Patchouli Oil | 200 |
| Bergamot Oil | 200 |
| 2-Ethyl-6,6-dimethyl-2-cyclohexen-1-carboxylic Acid Ethyl Ester | 100 |
| Estragol | 5 |
| Ethyl 3,4-dichloro-5-isothiazolecarboxylate | 25 |

The ethyl 3,4-dichloro-5-isothiazolecarboxylate enhances the woodiness, giving a more blended woody base.

| B. Fougere Base | Parts per thousand |
|---|---|
| Amyl Salicylate | 130 |
| Aubepine | 50 |
| Benzoin Siam Soluble Resin | 30 |
| Benzyl Acetate Extra | 100 |
| Bergamot 65 GD | 350 |
| Coumarin | 20 |
| DPG | 28 |
| Folrosia ®* | 10 |
| Geranium Bourbon | 30 |
| Heliotropin Crystals | 50 |
| Lavandin Oil | 40 |
| Lemarome Citral | 2 |
| Musk Ambrette | 30 |
| Nerol Prime | 10 |
| Phenyl Ethyl Alcohol | 30 |
| Trreemoss 50% DPG | 4 |
| Thymol 10% PDG | 1 |
| Vanillin U.S.P. | 5 |
| Ethyl 3,4-dichloro-5-isothiazolecarboxylate | 70 |

*Registered Trademark of Givaudan Corporation for p-isopropylcyclohexanol.

The ethyl 3,4-dichloro-5-isothiazolecarboxylate gives a sweeter blended rounded effect to the base.

What is claimed is:

1. A perfume base comprising an olfactory effective amount of ethyl 3,4-dichloro-5-isothiazolecarboxylate and at least one other odorant.

2. The perfume base of claim 1 wherein the amount of ethyl 3,4-dichloro-5-isothiazolecarboxylate ranges from about 1 to 200 parts per thousand by weight of the total perfume base.

3. The perfume base of claim 1 wherein the base has been diluted with 5 to 7 times its weight of an alcoholic diluent thereby providing a perfume.

4. The perfume base of claim 1 wherein the base has been diluted with 20 to 35 times its weight of an alcoholic diluent thereby providing a toilet water.

5. A method for improving the odor of perfume compositions which comprises adding thereto a proportion of ethyl 3,4-dichloro-5-isothiazolecarboxylate.

* * * * *